United States Patent [19]

Timpl

[11] 4,312,853
[45] Jan. 26, 1982

[54] RADIOIMMUNOLOGICAL DETERMINATION OF PROCOLLAGEN (TYPE III) AND PROCOLLAGEN PEPTIDE (TYPE III)

[75] Inventor: Rupert Timpl, Krailling, Fed. Rep. of Germany

[73] Assignee: Max-Planck-Gesellschaft, Gottingen, Fed. Rep. of Germany

[21] Appl. No.: 30,042

[22] Filed: Apr. 13, 1979

[30] Foreign Application Priority Data

Apr. 18, 1978 [DE] Fed. Rep. of Germany ....... 2816841

[51] Int. Cl.³ .................... G01N 33/56; G01N 33/58; G01T 1/00; G01N 33/54
[52] U.S. Cl. .................................... 424/1; 23/230 B; 260/112 B; 424/12
[58] Field of Search .................. 260/112 B; 424/1, 12; 23/230 B

[56] References Cited

FOREIGN PATENT DOCUMENTS 4940 10/1979 European Pat. Off. ............... 424/1

OTHER PUBLICATIONS

Rohde et al., Chem. Abstracts, vol. 89, Jul. 3, 1978, Abstract #2657f.
Nowack et al., Chem. Abstracts, vol. 86, Jan. 31, 1977, Abstract #27023x.
Blackwell et al., Biochem. Biophys. Res. Comm., vol. 75, No. 1, 1977, pp. 94–101.

*Primary Examiner*—Christine M. Nucker
*Attorney, Agent, or Firm*—Sprung, Felfe, Horn, Lynch & Kramer

[57] ABSTRACT

For the radioimmunological determination of procollagen (type III) and procollagen peptide (type III) a certain amount of radioactively tagged procollagen (type III) or procollagen peptide (type III) and a highly specific anti-procollagen (type III) serum or anti-procollagen peptide (type III) serum are brought to reaction together with a sample of an unknown content of procollagen (type III) or procollagen peptide (type III), the formed antigen-antibody complex is separated, desirably by the addition of a second antibody against the highly specific antiserum, and the radioactivity of the complex or of the supernatant liquid is measured. Highly purified procollagen peptide (type III) suitable for this purpose is obtained by the degradation of tissue or body fluids with collagenase and purification by immune adsorption and chromatography.

3 Claims, No Drawings

RADIOIMMUNOLOGICAL DETERMINATION OF PROCOLLAGEN (TYPE III) AND PROCOLLAGEN PEPTIDE (TYPE III)

The invention concerns a method for the radioimmunological determination of procollagen (type III) and procollagen peptide (type III) and the preparation of a procollagen peptide (type III) which is suitable for this method.

Procollagen (type III) is a biosynthetic precursory form of a special collagen (type III) which occurs mainly in the reticular connective tissue. It differs from collagen (type III) by having an additional peptide segment (procollagen peptide [type III]) located at the amino end, which can be split off from the molecule by treatment with collagenase.

Recent immunofluorescent research has shown that fibrotic processes which occur, for example, in cirrhosis of the liver and hepatitis, are accompanied by a high transformation of procollagen (type III) and procollagen peptide (type III). The detection of these antigens circulating in the blood therefore makes possible the early recognition of such diseases.

Immunohistological tests do permit a specific detection of these antigens, but they cannot be evaluated quantitatively. Consequently the information that can be obtained by such methods is limited.

The object of the invention, therefore, is to solve this problem and create a quantitative method, which is quick and simple to practice, for determining these antigens.

It has been found that a quantitative measurement of such antigens can be accomplished by a radioimmunological method of determination.

Subject matter of the invention, therefore, is a method for the radioimmunological determination of procollagen (type III) and procollagen peptide (type III), in which a certain amount of radioactively tagged procollagen (type III) or procollagen peptide (type III) and a highly specific antiprocollagen (type III) serum or an antiprocollagen peptide (type III) serum are made to react together with a specimen having an unknown content of procollagen (type III) or procollagen peptide (type III). In the manner which is known in the radioimmuno assay (RIA), the radioactively tagged procollagen or procollagen peptide competes with the untagged procollagen or procollagen peptide contained in the sample for the antibody, so that the greater the content of untagged procollagen or procollagen peptide is in the sample being determined, the lower the radioactivity will be in the antigen-antibody complex that is formed. The insoluble antigen-antibody complex can then be separated from the solution and the radioactivity it contains can be determined in a conventional manner. Alternatively, it is also possible to measure the radioactivity remaining in the solution, i.e., in the liquid remaining after separation of the antigen-antibody complex. With the aid of a calibration curve established by means of samples having a known content of procollagen or procollagen peptide, it is then possible to determine the quantity of procollagen or procollagen peptide that is contained in the sample being tested.

The separation of the antigen-antibody complex from the solution can be performed by conventional methods known to the technical expert, such as filtration, suction filtration, centrifugal separation and the like. It is also possible to have the antiserum bound to a solid support, such as for example the inside wall of a test tube.

Preferably, the method is practiced by separating the antigen-antibody complex formed with the highly specific antiprocollagen (type III) serum or with the antiprocollagen peptide (type III) serum from the unreacted antigen with by using a second antibody against the highly specific serum. Preferred for this purpose is an antibody against gamma immunoglobulin obtained from the type of animal used for the production of the antiserum.

The tagging of the antigen, i.e., of the procollagen (type III) or procollagen peptide (type III), with the radionuclide can be performed by the methods known in the radioactive tagging of proteins. Iodine 125 is used preferentially as the radionuclide. The chloramine-T method (Int. Arch. Allergy, 29, 185) is preferred for tagging with this radionuclide.

For the method of determination according to the invention it is essential that a suitable source be available for the production of procollagen peptide (type III). It has been found that the preparation of human or animal, highly refined procollagen peptide (type III) from animal tissue or pathological body fluids can be accomplished if the tissue is degraded with collagenase and the procollagen or procollagen peptide is separated from the collagenase extract or from the body fluid and purified by a combination of chromatographic methods and/or immunoadsorption.

Additional subject matter of the invention, therefore, is a method of preparing a highly refined procollagen peptide (type III) suitable for the determination method of the invention, which is characterized by the fact that human or animal tissue or pathological body fluid or collagen extracts of same are degraded with collagenase and the procollagen or procollagen peptide thus formed is separated from the collagenase extract or from the body fluid and purified chromatographically or by immunoadsorption or by a combination of these methods.

Fetal calf hide has proven to give good results as animal tissue, and human ascites as body fluid, for the production of procollagen peptide (type III).

Purification by immunoadsorption is best performed as follows: In a first step, purified antibodies to procollagen peptide (type III) are rendered insoluble. The purification of the antibodies is best performed by affinity chromatography, although other methods known for the purification of antibody can be used. Antibodies obtained from rabbits are preferred. Insolubilization is accomplished by fixation on a solid support by the known methods for the fixation of biologically active proteins to solid supports. Preferably the antibodies are bound to agarose activated with bromocyan or diazotized p-aminobenzylcellulose. With the antibody adsorber thus prepared the extracts or body fluids, after preliminary purification if desired, are then incubated. The procollagen peptide (type III) will attach itself to the antibody adsorber and then, preferably after washing the support, it will be eluted again with appropriate eluents. The suitable eluents can easily be determined by simple preliminary testing. Approximately 3x molar KSCN solution has proven especially suitable for the elution, although, of course, other salt solutions can be used.

The purified procollagen peptide (type III) thus prepared is then used for the immunization, and thus a highly specific antiprocollagen peptide (type III) serum is prepared by the common methods of antiserum production. The immunization is best performed by the subcutaneous injection of procollagen peptide (type III) into test animals, preferably rabbits, in the presence of the complete Freund adjuvant. In this preferred case, the antigen dose should be approximately 2 milligrams per animal.

The radioimmune test of the invention permits the measurement of concentrations into the range of 1 nanogram per milliliter. This makes it possible to use the test for the determination of antigen in human serums. A comparison of probands with fibrosis of the liver revealed as much as a tenfold increase in the concentration of the antigen, whereby liver diseases can be reliably diagnosed.

The following examples further explain the invention.

EXAMPLE 1

Performance of the Radioimmune Test:

25 micrograms of procollagen peptide (type III) are tagged with 1 millicurie of iodine 125 by the chloramine-T method and unbound iodine is removed by dialysis. The rest of the steps in the preparation of the radioimmune test are performed preferably in the presence of 0.04% of a nonionic detergent, such as Tween 20 for example. Curves representing binding with antibody are determined with 2 nanograms of tagged peptide. The procollagen peptide (type III) concentration in an unknown sample of serum or other body fluids is determined in the following inhibition test: A specific amount of the antibody is pre-incubated with the unknown sample for 6 hours at 4° C.; 2 ng of tagged peptide is added and the mixture is incubated for another 12 hours at 4° C. Then an excess of antibody against rabbit gamma immunoglobulin is added and the antigen bound in the immune complex is separated from the solution. The inhibition activity of the unknown sample is compared with the activity of a standard concentration of untagged procollagen peptide (type III).

EXAMPLE 2

Preparation of Procollagen Peptide (Type III):

Procollagen peptide (type III) is prepared by the action of collagenase on procollagen (type III) at 37° C. The peptide is not exposed to any denaturing agents. A modified method is used for the preparation of larger amounts of the peptide. All steps of the process except that of the action of the collagenase on [the procollagen] is performed in the refrigerated room. The various NaCl solutions which are used for the solubilization contain 0.05 M tris-HCl, pH 7.4, 0.01 M EDTA, sodium azide (200 mg/ml) and the protease inhibitors phenylmethylsulfonyl fluoride (3 $\mu$g/ml) and p-chloromercury benzoate (3 $\mu$g/ml).

Fetal calf hide (3 kg) is homogenized in 10 liters of a molar solution of NaCl and extracted for two days. Dissolved collagen is precipitated from the extract by the addition of solid NaCl to a final concentration of 2.5 M. After stirring overnight, the precipitate is collected by centrifugation (1800 xg, 20 minutes), washed twice with 2.5 M NaCl, and redissolved by stirring it overnight in 10 liters of 0.5 M NaCl. Small amounts of insoluble material are removed by centrifugation. The mixture of collagen (type III) and procollagen (type III) thus obtained is then precipitated with 1.6 M NaCl. The precipitate is then suspended in 2 liters of 0.05 M tris-HCl (pH 8.0) and, after the addition of 0.02 M $CaCl_2$, it is heated at 50° C. for 20 minutes and then incubated at 37° C. for 3 hours with 1500 units of bacterial collagenase per gram of moist precipitate. After the collagenase has acted, the precipitate that has formed is separated by centrifugation and the solution is dialyzed against 0.005 M tris-HCl, pH 8.6, and 8 M urea and placed on a DEAE cellulose column (5.0×30 cm) which has been balanced with the same buffer.

The proteins bound on the column are washed out with NaCl solutions whose concentration increases from 0 to 0.3 M. The total elution volume amounts to 2 liters. The solution flowing out of the column is tested for adsorption at 236 nm and for its antigen activity by the use of antibodies which are specific for the aminoterminal segment of the type III procollagen. Normally, the last peak that is eluted from the column contains the procollagen peptide (type III). The peptide is desalted by dialysis against distilled water and lyophilized. Further purification is performed with agarose A 1.5 M in a column (2×120 cm), which is balanced with 1 M $CaCl_2$, 0.05 M tris-HCl, pH 7.5.

I claim:

1. Method for the radioimmunological determination of procollagen (type III) and procollagen peptide (type III), which method comprises reacting a sample having a unknown content of procollagen (type III) or procollagen peptide (type III) with a defined amount of radioactively tagged procollagen (type III) or procollagen peptide (type III) and a highly specific anti-procollagen (type III) serum or anti-procollagen peptide (type III) serum, separating the antigen anti-body complex formed, and measuring the radioactivity of the complex or of the super-natant liquid as a measure of the content of procollagen (type III) or procollagen peptide (type III) in said sample.

2. Method as claimed in claim 1 wherein iodine 125 is used as the radioactive tag.

3. Method as claimed in claim 1 wherein the antigen-antibody complex formed from anti-procollagen (type III) serum or anti-procollagen peptide (type III) serum and procollagen (type III) or procollagen peptide (type III), as the case may be, is separated from unreacted antigen by the addition of a second antibody against the highly specific anti-serum and separation from the super-natant liquid of the complex thus formed.

* * * * *